US009145318B2

(12) United States Patent
Rohde

(10) Patent No.: US 9,145,318 B2
(45) Date of Patent: Sep. 29, 2015

(54) SYSTEMS AND METHODS FOR REMOVING HYDROGEN PEROXIDE FROM WATER PURIFICATION SYSTEMS

(75) Inventor: Justin B. Rohde, Des Plaines, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 158 days.

(21) Appl. No.: 13/110,496

(22) Filed: May 18, 2011

(65) Prior Publication Data
US 2011/0284377 A1 Nov. 24, 2011

Related U.S. Application Data

(60) Provisional application No. 61/347,520, filed on May 24, 2010.

(51) Int. Cl.
 *B01D 61/44* (2006.01)
 *B01D 61/46* (2006.01)
 (Continued)

(52) U.S. Cl.
 CPC ............... *C02F 9/00* (2013.01); *A61M 1/1656* (2013.01); *B01J 23/02* (2013.01); *B01J 23/06* (2013.01); *B01J 23/34* (2013.01); *B01J 23/72* (2013.01); *B01J 23/745* (2013.01); *C02F 1/4695* (2013.01); *B01D 61/48* (2013.01); *B01D 61/52* (2013.01);
 (Continued)

(58) Field of Classification Search
 CPC ........ A61M 1/1656; B01J 23/02; B01J 23/06; B01J 23/34; B01J 23/72; B01J 23/745; C02F 1/4695; C02F 2103/04; C02F 2201/4618; C02F 2303/18; C02F 9/00; C02F 1/42; C02F 2001/422–2001/427; C02F 1/46–1/4698; C02F 2201/46–2201/46195; B01D 59/38–59/42; B01D 61/42–61/56; B01D 2311/2684; B01D 2325/42; B01D 2253/206; B01D 2311/2623
 USPC ......... 210/627, 631, 638, 660, 673, 757, 758, 210/759, 542, 198.1; 204/524, 527, 533, 204/536, 540, 632
 See application file for complete search history.

(56) References Cited

U.S. PATENT DOCUMENTS 5,244,568 A 9/1993 Lindsay et al.
5,350,357 A 9/1994 Kamen et al.
(Continued)

FOREIGN PATENT DOCUMENTS

GB  2 396 625   6/2004
WO  03/040042   5/2003
(Continued)

OTHER PUBLICATIONS

International Preliminary Report for Patentability for Application No. PCT/US2011/036924 dated Aug. 20, 2012.
(Continued)

*Primary Examiner* — David C Mellon
*Assistant Examiner* — Pranav Patel
(74) *Attorney, Agent, or Firm* — K&L Gates LLP

(57) ABSTRACT

Systems and methods for removing hydrogen peroxide from water purification systems are provided. In a general embodiment, the present disclosure provides a water purification system including a water treatment unit, an electrodeionization unit and a hydrogen peroxide decomposition catalyst in fluid connection with the electrodeionization unit. The water purification system can be fluidly connected to a renal treatment system.

13 Claims, 2 Drawing Sheets

(51) Int. Cl.
*C02F 1/469* (2006.01)
*C02F 9/00* (2006.01)
*A61M 1/16* (2006.01)
*B01J 23/02* (2006.01)
*B01J 23/06* (2006.01)
*B01J 23/34* (2006.01)
*B01J 23/72* (2006.01)
*B01J 23/745* (2006.01)
*B01D 61/52* (2006.01)
*B01D 61/48* (2006.01)
*C02F 103/04* (2006.01)

(52) U.S. Cl.
CPC ..... *B01D 2311/08* (2013.01); *B01D 2311/2696* (2013.01); *C02F 2103/04* (2013.01); *C02F 2201/4618* (2013.01); *C02F 2303/18* (2013.01)

(56) References Cited

U.S. PATENT DOCUMENTS

| | | |
|---|---|---|
| 5,662,806 A | 9/1997 | Keshaviah et al. |
| 5,873,853 A | 2/1999 | Keilman et al. |
| 5,984,891 A | 11/1999 | Keilman et al. |
| 6,196,992 B1 | 3/2001 | Keilman et al. |
| 6,379,518 B1* | 4/2002 | Osawa et al. ............... 204/524 |
| 6,592,542 B2 | 7/2003 | Childers et al. |
| 6,824,662 B2* | 11/2004 | Liang et al. ............... 204/524 |
| 7,318,892 B2 | 1/2008 | Connell et al. |
| 2006/0243604 A1* | 11/2006 | Nakagawa et al. ........... 205/775 |
| 2007/0221581 A1* | 9/2007 | Kitami et al. ............... 210/748 |
| 2008/0067125 A1* | 3/2008 | Wilkins et al. ............... 210/641 |
| 2010/0051552 A1* | 3/2010 | Rohde et al. ............... 210/647 |

FOREIGN PATENT DOCUMENTS

| | | |
|---|---|---|
| WO | 03/105424 | 12/2003 |
| WO | 2004096717 | 11/2004 |
| WO | 2005038091 | 4/2005 |
| WO | 2010/024963 | 3/2010 |

OTHER PUBLICATIONS

European Office Action for European Application No. 11 726 535.5. dated Jul. 16, 2014.

* cited by examiner

SYSTEMS AND METHODS FOR REMOVING HYDROGEN PEROXIDE FROM WATER PURIFICATION SYSTEMS

PRIORITY CLAIM

This application claims the benefit of U.S. Provisional Patent Application Ser. No. 61/347,520 filed on May 24, 2010, the entire disclosure of which is hereby incorporated by reference.

BACKGROUND

The present disclosure generally relates to water purification systems. More specifically, the present disclosure relates to systems and methods for removing hydrogen peroxide from water purification systems used in renal treatment systems.

Water purification systems can be used in a variety of applications. For example, water purification systems can be used to feed purified water to a dialysis treatment system. A hemodialysis system uses fresh fluid from a solution bag or a water purification system to generate dialysis fluid that is used to dialyze a patient. Water purification systems can be built from many different technologies such as, for example, an electrodeionization ("EDI") unit having an electrodeionizer to obtain extremely pure water.

EDI units typically generate two streams of water—a treated water stream and a waste water stream. The treated water stream is extremely pure water that is substantially free of electrolytes. The treated water stream is used as the source water for other applications requiring purified water. The waste water stream may contain electrolytes and, depending on the design of the device, may have hydrogen peroxide as a byproduct of the EDI process. In this case, the waste water stream is usually emptied to a drain and discarded to prevent the hydrogen peroxide from being part of the treated water stream. However, discarding the waste water stream decreases the efficiency of the EDI for purifying water as approximately 25% of the water flow into a typical EDI unit becomes part of the waste water stream.

SUMMARY

The present disclosure relates to systems and methods for removing hydrogen peroxide from water purification systems. In a general embodiment, the present disclosure provides a water purification system including a water treatment unit, an EDI unit and a hydrogen peroxide decomposition catalyst in fluid connection with the EDI unit.

The water purification system can be fluidly connected to a suitable renal treatment system. The renal treatment system can be for hemodialysis, hemofiltration, hemodiafiltration, automated peritoneal dialysis, continuous renal replacement therapy, continuous ambulatory peritoneal dialysis, continuous flow peritoneal dialysis and the like. It should be appreciated that alternative embodiments of the water purification systems can be used in any variety of different and suitable dialysis therapies to treat kidney failure.

In, an embodiment, the hydrogen peroxide decomposition catalyst includes Manganese Dioxide. In another embodiment, the hydrogen peroxide decomposition catalyst can be one or more of Silver, Catalase, Peroxidase, Potassium Iodide, Copper (II) Oxide, Zinc Oxide, Fe(2+), Ti(3+) or a combination thereof.

In another embodiment, the present disclosure provides a renal treatment system including a water treatment unit, an EDI unit, and a hydrogen peroxide decomposition catalyst in fluid connection with the EDI unit and positioned downstream of the EDI unit. The water treatment unit can include an activated carbon unit, a sediment filter, a softening unit, a sorbent, an ultra-violet unit, a membrane filter, a distilling unit, a deionization unit or a combination thereof.

In an alternative embodiment, the present disclosure provides a water purification system including a water treatment unit and a hydrogen peroxide decomposition catalyst. The water treatment unit can include an activated carbon unit, a sediment filter, a softening unit, a sorbent, an ultra-violet unit, a membrane filter, a distilling unit, a deionization unit or a combination thereof.

In still another embodiment, the present disclosure provides a method of purifying water. The method comprises passing water through a water treatment unit, passing the water through an EDI unit to produce a rejected water stream, passing the rejected water stream through a hydrogen peroxide decomposition catalyst, and recirculating the rejected water stream back through the water treatment unit. The water treatment unit can include an activated carbon unit, a sediment filter, a softening unit, a sorbent, an ultra-violet unit, a membrane filter, a distilling unit, a deionization unit or a combination thereof.

In an alternative embodiment, the present disclosure provides a method of performing dialysis. The method comprises passing water through a water treatment unit, passing the water through an EDI unit. The EDI unit produces a rejected water stream and a purified water stream. The purified water stream is passed to a renal treatment system. The rejected water stream passed through a hydrogen peroxide decomposition catalyst and recirculated back to the water treatment unit.

In yet another embodiment, the present disclosure provides a method of preventing the formation of bacterial contamination in a water purification system while performing dialysis. The method comprises passing water through a circuit of a water treatment unit to produce a purified water stream, adding hydrogen peroxide to the purified water stream to circulate through the circuit, and passing the purified water stream having the hydrogen peroxide through a unit having a hydrogen peroxide decomposition catalyst. The added hydrogen peroxide can be from an EDI unit or other source. The purified water stream/hydrogen peroxide mixture can be passed to a suitable renal treatment system but includes a hydrogen peroxide decomposition catalyst that decomposes the hydrogen peroxide prior to use in a renal treatment system.

An advantage of the present disclosure is to provide an improved water purification system for use with a renal treatment system.

Another advantage of the present disclosure is to provide a water purification system having reduced water consumption.

Yet another advantage of the present disclosure is to provide a water purification system having reduced operating costs.

Still another advantage of the present disclosure is to provide an improved method of removing hydrogen peroxide from a water purification system having an EDI unit.

Another advantage of the present disclosure is to provide an improved method of removing a hydrogen peroxide disinfectant from a water purification system during use with a renal treatment system.

Additional features and advantages are described herein, and will be apparent from, the following Detailed Description and the figures.

DETAILED DESCRIPTION

The present disclosure relates to systems and methods for removing hydrogen peroxide from a water purification system. Current water purification systems that use hydrogen peroxide as a disinfectant require extensive rinsing and chemical testing to ensure that all of the residual disinfectant has been removed from the system prior to use.

Water purification systems may include EDI units to further achieve extremely pure water. It has recently been found that some EDI units, depending on their particular design, can generate hydrogen peroxide. In these cases, the hydrogen peroxide is found as a byproduct in the waste water stream of the EDI units and must be discarded rather than reused or recycled within the water purification system to prevent the hydrogen peroxide from reaching the clean product water stream. Discarding the waste water stream having the hydrogen peroxide can drastically reduce the efficiency of the water purification system and increase the operating costs.

Embodiments of the present disclosure are directed to systems and methods to efficiently and effectively recycle the waste water stream from the EDI unit back through the water purification system thereby decreasing or removing the need to discard the waste water stream from the EDI unit. Because the waste water stream generated by the EDI unit is still appropriate for use as feed water to other purification components within the water purification system, such as a reverse osmosis membrane or a distilling unit, the waste water stream of the EDI unit can be recycled to feed the purification components in lieu of drawing additional feed water from a feed water source such as a tap or faucet. As a result, most if not all of the water that enters the EDI unit can be converted into extremely pure product water for suitable applications such as dialysis treatment technologies.

The water purification systems and methods in embodiments of the present disclosure can be utilized and implemented in various renal treatment systems. Such renal treatment systems are described in U.S. Pat. Nos. 5,244,568, 5,350,357, 5,662,806, 6,592,542 and 7,318,892, which are incorporated herein by reference. The water purification systems and methods can further be utilized in portable dialysis devices such as, for example, wearable artificial kidneys in which a patient may move freely during dialysis. The portable dialysis devices can also encompass transportable dialysis devices (e.g., dialysis devices that are sized to be transported by a user), which are not need to be fixed in one place such as a hospital. Portable dialysis devices are described in U.S. Pat. Nos. 6,196,992, 5,873,853 and 5,984,891, which are incorporated herein by reference. The water purification systems and methods can be used in medical centers or be implemented with on-site or at-home dialysis treatments.

Figure 1:
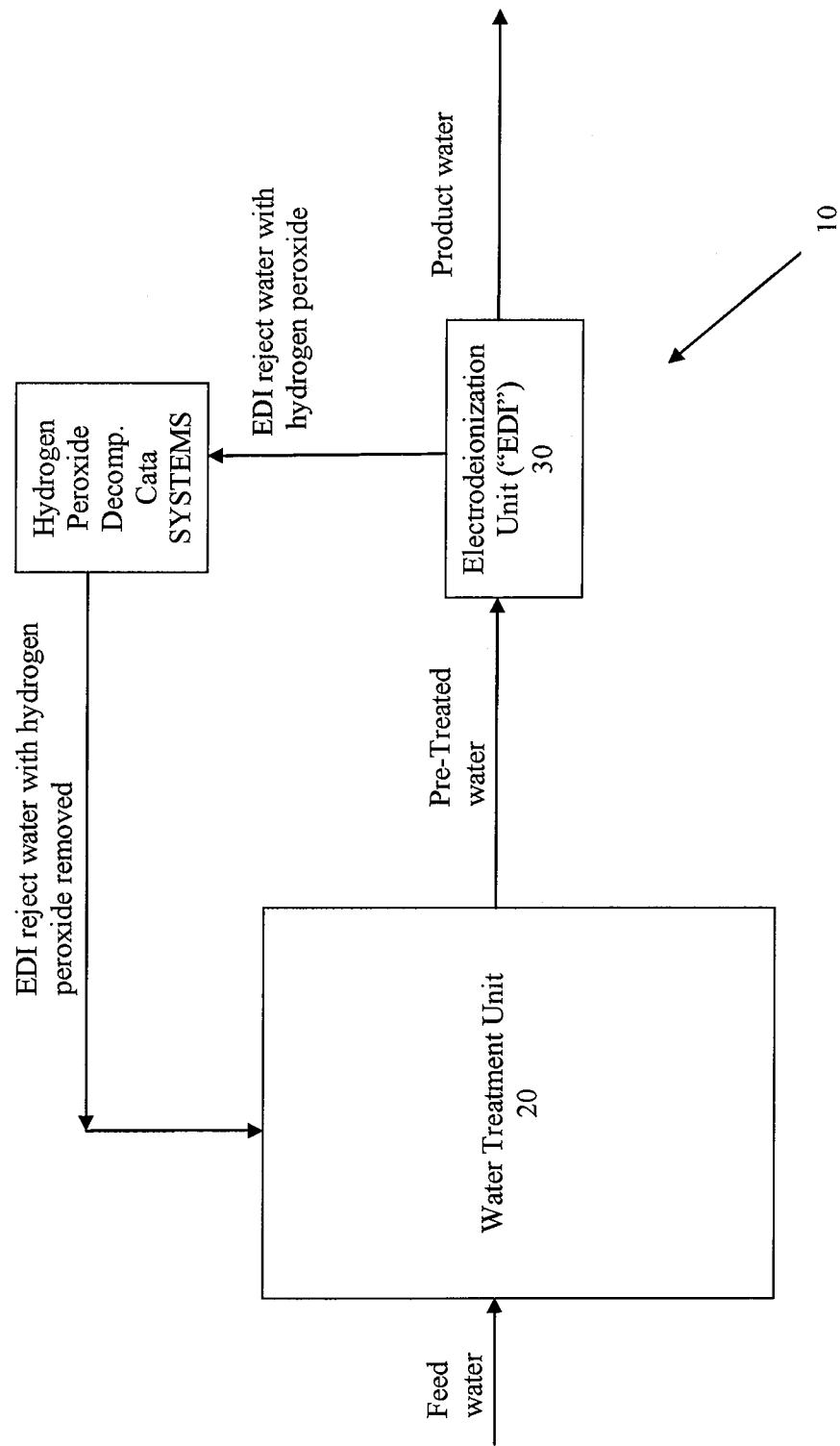
FIG. 1 illustrates a schematic of a water purification system in an embodiment of the present disclosure.

In a general embodiment illustrated in FIG. 1, the present disclosure provides a water purification system 10 including a water treatment unit 20, an EDI unit 30 and a hydrogen peroxide decomposition catalyst 40 in fluid connection with EDI unit 30. Hydrogen peroxide decomposition catalyst 40 can take the form, for example, of beads/particles in a filter bed, be free floating in a fluid stream of water purification system 10, and/or be part of a mechanical structure in the fluid stream (e.g., a screen/mesh). Alternatively, any tubing of water purification system 10 could be made to include the hydrogen peroxide decomposition catalyst 40, for example, along an inner wall that is in contact with the fluid flowing through.

Water treatment unit 20 can include any suitable components for cleaning water such as an activated carbon unit, a sediment filter, a softening unit, a sorbent, an ultra-violet unit, a membrane filter, a distilling unit, a deionization unit and combinations thereof. The membrane filters can include ultrafiltration membranes and reverse osmosis membranes.

Hydrogen peroxide decomposition catalyst 40 can be positioned downstream of a waste or rejected water stream of EDI unit 30. Clean product water from EDI unit 30 can be sent to a variety of applications that require purified water. For example, the clean product water can be a source of purified water for a dialysis treatment system or other infusion system.

EDI unit 30 generates a secondary rejected water stream as a result of the EDI process as seen in FIG. 1. It is this rejected water stream that passes through hydrogen peroxide decomposition catalyst 40 and can be recycled back to water treatment unit 20. Recycling this water reduces water consumption and reduces consumption of the purification components, for example, in the water treatment unit 20.

An electrodeionizer is an electrodialyzer in which the diluate channel into which water treated in water treatment unit 20 is introduced is filled with a bed of mixed ion exchange resin beads. At the top of the channel where the feed solution is introduced, the electrolytes present in the treated water carry the current. Even though the ion exchange resin beads are there, they do not serve much of a deionization function. The mixed ion exchange resin beads in the electrodeionizer do not remove electrolytes themselves, but are used to alleviate the effects of water splitting as a result of little to no electrolytes remaining in the solution further down the channel.

As the water moves down the length of the diluate chamber, there may not be much of the feed solution electrolyte left. The current is carried out in these sections of the diluate chamber by protons and hydroxyl ions generated by the ion exchange resin beads. The proton goes through a cation exchange membrane and forms water by combining with hydroxyl ions that have come from an alternate anion exchange membrane. Similarly, the hydroxyl ion goes through an anion exchange membrane and combines with a proton that comes from an alternate anion exchange membrane. The resultant purified water has almost no electrolytes left and results in an extremely pure water stream.

The rejected water stream, which may include hydrogen peroxide, can be passed through hydrogen peroxide decomposition catalyst 40. In an embodiment, hydrogen peroxide decomposition catalyst 40 is in the form of a cartridge or capsule that includes the catalyst and allows water to pass through. As a result, any hydrogen peroxide in the water can be removed or degraded as the water passes through hydrogen peroxide decomposition catalyst 40. In an embodiment, hydrogen peroxide decomposition catalyst 40 can include an amount of the catalyst that corresponds to an amount ranging from about 10 mL to about 100 mL of catalyst for each 250 mL/min of water flow through the catalyst.

The hydrogen peroxide decomposition catalyst in any embodiments described herein can include any suitable catalyst that degrades or decomposes hydrogen peroxide, for example, into water and oxygen. In an embodiment, the hydrogen peroxide decomposition catalyst includes Manganese Dioxide, for example, in a granular form. In another embodiment, the hydrogen peroxide decomposition catalyst can be one or more of Silver, Catalase, Peroxidase, Potassium Iodide, Copper (II) Oxide, Zinc Oxide, $Fe(2+)$, $Ti(3+)$ and combinations thereof.

Water purification system 10 can be fluidly connected to any suitable renal treatment system. Non-limiting examples of such a renal treatment system include hemodialysis, hemofiltration, hemodiafiltration, automated peritoneal dialysis, continuous renal replacement therapy, continuous ambulatory peritoneal dialysis, continuous flow peritoneal dialysis and the like. The renal treatment system can include any suitable dialysis components including, but not limited to, a dialyzer, pumps, temperature monitors and fluid heaters, conductivity meters, flow meters, extracorporeal circuits, etc.

Figure 2:
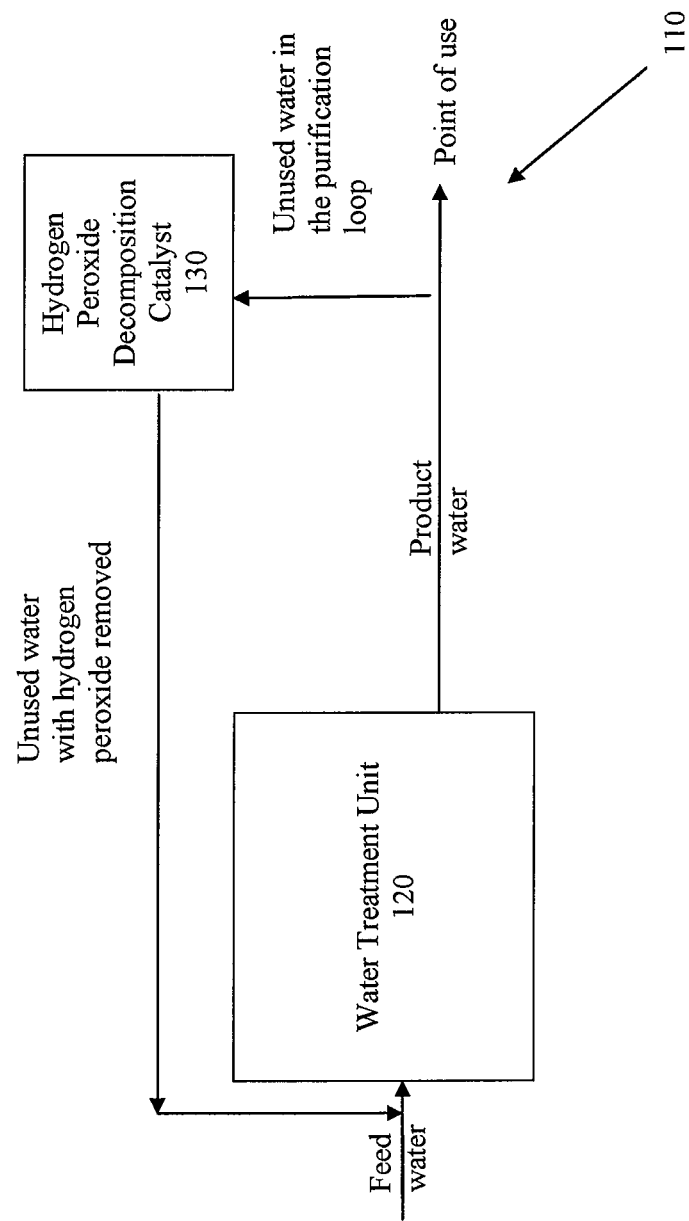
FIG. 2 illustrates a schematic of a water purification system in another embodiment of the present disclosure.

In an alternative embodiment shown in FIG. 2, the present disclosure provides a water purification system 110 including a water treatment unit 120, and a hydrogen peroxide decomposition catalyst 130 in fluid connection with water treatment unit 120. Water treatment unit 120 can include any suitable components for cleaning water such as an activated carbon unit, a sediment filter, a softening unit, a sorbent, an ultraviolet unit, a membrane filter, a distilling unit, a deionization unit and combinations thereof. The membrane filters can include ultrafiltration membranes and reverse osmosis membranes.

In this embodiment, water purification system 110 can utilize hydrogen peroxide as a cleaning source to disinfect water purification system 110. Hydrogen peroxide can be added to water that is used to flush out water purification system 110 and any systems attached to water purification system 110. Once water purification system 110 has been disinfected, hydrogen peroxide decomposition catalyst 130 can remove or degrade any residual hydrogen peroxide remaining in water purification system 110.

In an alternative embodiment, the present disclosure provides a home hemodialysis system. For example, the home hemodialysis unit can be a self-contained hemodialysis system designed to treat a single individual. The home hemodialysis can also be portable. The home hemodialysis system includes a water treatment unit, an electrodeionization unit, and a hydrogen peroxide decomposition catalyst in fluid connection with the electrodeionization unit and positioned downstream of the electrodeionization unit. A dialyzer is in fluid connection with the electrodeionization unit.

In still another embodiment, the present disclosure provides a method of purifying water. The method comprises passing water through a water treatment unit to receive a first cleaning treatment. The source of the water can be tap water or water that has already been partially purified by other purification components. The treated water is then passed through an EDI unit to produce the final purified product water. The EDI unit also produces a rejected water stream that is then passed through a hydrogen peroxide decomposition catalyst and recirculated back through the water treatment unit. The water treatment unit can include an activated carbon unit, a sediment filter, a softening unit, a sorbent, an ultraviolet unit, a membrane filter, a distilling unit, a deionization unit or a combination thereof.

In an alternative embodiment, the present disclosure provides a method of performing dialysis. The method comprises passing water through a water treatment unit. The source of the water can be tap water or water that has already been partially purified by other purification components. The treated water exiting the water treatment unit can be passed through an EDI unit to produce a rejected water stream and a purified water stream. The purified water stream is passed to a suitable renal treatment system. The rejected water stream is passed through a hydrogen peroxide decomposition catalyst and recirculated back to the water treatment unit. Recycling the rejected water stream reduces water consumption and reduces consumption of the purification components, for example, that are part of the water treatment unit.

In yet another embodiment, the present disclosure provides a method of disinfecting a water purification system. The method comprises passing water through a circuit of the water purification system. The source of the water can be tap water or water that has already been partially purified by other purification components. Hydrogen peroxide can be added to the water to circulate throughout the circuit. While the disinfecting water having the hydrogen peroxide is flushed out of the circuit, the disinfecting water can be passed through a unit having a hydrogen peroxide decomposition catalyst.

In another embodiment, the present disclosure provides a method of preventing the formation of bacterial contamination in a water purification system during dialysis. The method comprises passing water through a circuit of a water treatment unit. Within this system, hydrogen peroxide is added to the fluid stream, either from a reservoir or through generation by an EDI or other suitable generator. This hydrogen peroxide can reside in the water of the fluid stream through the distribution up to the point of use thereby eliminating bacterial contamination in the system.

Prior to use in a renal treatment system or otherwise, the hydrogen peroxide is decomposed into water and oxygen by a hydrogen peroxide decomposition catalyst as described in any of the embodiments herein thereby ensuring that the purity of the fluid at the point of use is maintained. For example, the fluid stream can be circulated in the circuit passing through the hydrogen peroxide decomposition catalyst until the hydrogen peroxide has sufficiently decomposed.

Aspects of the Present Disclosure

Aspects of the subject matter described herein may be useful alone or in combination one or more other aspect described herein. Without limiting the foregoing description, in a first aspect of the present disclosure, a water purification system includes: a water treatment unit, an electrodeionization unit, and a hydrogen peroxide decomposition catalyst in fluid connection with the electrodeionization unit.

In accordance with a second aspect of the present disclosure, which may be used in combination with the first aspect, the hydrogen peroxide decomposition catalyst includes Manganese Dioxide.

In accordance with a third aspect of the present disclosure, which may be used in combination with any one or more of the preceding aspects, the hydrogen peroxide decomposition catalyst is selected from the group consisting of Silver, Catalase, Peroxidase, Potassium Iodide, Copper (II) Oxide, Zinc Oxide, Fe(2+), Ti(3+) and combinations thereof.

In accordance with a fourth aspect of the present disclosure, which may be used in combination with any one or more of the preceding aspects, the water purification system further includes a dialyzer in fluid connection with the electrodeionization unit.

In accordance with a fifth aspect of the present disclosure, which may be used in combination with any one or more of the preceding aspects, a renal treatment system includes: a water treatment unit, an electrodeionization unit, a hydrogen peroxide decomposition catalyst in fluid connection with the electrodeionization unit and positioned downstream of the electrodeionization unit, and a dialyzer in fluid connection with the electrodeionization unit.

In accordance with a sixth aspect of the present disclosure, which may be used with any one or more of the preceding aspects in combination with the fifth aspect, the water treatment unit includes a component selected from the group consisting of an activated carbon unit, a sediment filter, a softening unit, a sorbent, an ultra-violet unit, a membrane filter, a distilling unit, a deionization unit and combinations thereof.

In accordance with a seventh aspect of the present disclosure, which may be used with any one or more of the preceding aspects in combination with the fifth aspect, the hydrogen peroxide decomposition catalyst includes Manganese Dioxide.

In accordance with an eighth aspect of the present disclosure, which may be used with any one or more of the preceding aspects in combination with the fifth aspect, the hydrogen peroxide decomposition catalyst is selected from the group consisting of Silver, Catalase, Peroxidase, Potassium Iodide, Copper (II) Oxide, Zinc Oxide, Fe(2+), Ti(3+) and combinations thereof.

In accordance with a ninth aspect of the present disclosure, which may be used in combination with any one or more of the preceding aspects, a water purification system includes: a water treatment unit, and a hydrogen peroxide decomposition catalyst in fluid communication with the water treatment unit.

In accordance with a tenth aspect of the present disclosure, which may be used with any one or more of the preceding aspects in combination with the ninth aspect, the hydrogen peroxide decomposition catalyst includes Manganese Dioxide.

In accordance with an eleventh aspect of the present disclosure, which may be used with any one or more of the preceding aspects in combination with the ninth aspect, the hydrogen peroxide decomposition catalyst is selected from the group consisting of Silver, Catalase, Peroxidase, Potassium Iodide, Copper (II) Oxide, Zinc Oxide, Fe(2+), Ti(3+) and combinations thereof.

In accordance with a twelfth aspect of the present disclosure, which may be used with any one or more of the preceding aspects in combination with the ninth aspect, the water treatment unit includes a component selected from the group consisting of an activated carbon unit, a sediment filter, a softening unit, a sorbent, an ultra-violet unit, a membrane filter, a distilling unit, a deionization unit and combinations thereof.

In accordance with a thirteenth aspect of the present disclosure, which may be used in combination with any one or more of the preceding aspects, a home hemodialysis system includes: a water treatment unit, an electrodeionization unit, a hydrogen peroxide decomposition catalyst in fluid connection with the electrodeionization unit and positioned downstream of the electrodeionization unit, and a dialyzer in fluid connection with the electrodeionization unit.

In accordance with a fourteenth aspect of the present disclosure, which may be used with in combination with any one or more of the preceding aspects, a method of purifying water comprises: passing water through a water treatment unit, passing the water through an electrodeionization unit to produce a rejected water stream, passing the rejected water stream through a hydrogen peroxide decomposition catalyst, and recirculating the rejected water stream back through the water treatment unit.

In accordance with a fifteenth aspect of the present disclosure, which may be used with any one or more of the preceding aspects in combination with the fourteenth aspect, the hydrogen peroxide decomposition catalyst includes Manganese Dioxide.

In accordance with a sixteenth aspect of the present disclosure, which may be used with any one or more of the preceding aspects in combination with the fourteenth aspect, the hydrogen peroxide decomposition catalyst is selected from the group consisting of Silver, Catalase, Peroxidase, Potassium Iodide, Copper (II) Oxide, Zinc Oxide, Fe(2+), Ti(3+) and combinations thereof.

In accordance with a seventeenth aspect of the present disclosure, which may be used with any one or more of the preceding aspects in combination with the fourteenth aspect, the water treatment unit includes a component selected from the group consisting of an activated carbon unit, a sediment filter, a softening unit, a sorbent, an ultra-violet unit, a membrane filter, a distilling unit, a deionization unit and combinations thereof.

In accordance with a eighteenth aspect of the present disclosure, which may be used with in combination with any one or more of the preceding aspects, a method of disinfecting a water purification system comprises: passing water through a circuit of a water purification system, adding hydrogen peroxide to the water to circulate through the circuit, and passing the water having the hydrogen peroxide through a unit having a hydrogen peroxide decomposition catalyst.

In accordance with a nineteenth aspect of the present disclosure, which may be used with in combination with any one or more of the preceding aspects, a method of performing dialysis comprises: passing water through a water treatment unit, passing the water through an electrodeionization unit, the electrodeionization unit producing a rejected water stream and a purified water stream, passing the purified water stream to a dialysis treatment system, and recirculating the rejected water stream through a hydrogen peroxide decomposition catalyst and back to the water treatment unit.

In accordance with a twentieth aspect of the present disclosure, which may be used with any one or more of the preceding aspects in combination with the nineteenth aspect, the method further comprises passing the purified water stream to a renal treatment system selected from the group consisting of hemodialysis, hemofiltration, hemodiafiltration, automated peritoneal dialysis, continuous ambulatory peritoneal dialysis and continuous flow peritoneal dialysis.

In accordance with a twenty-first aspect of the present disclosure, which may be used with any one or more of the preceding aspects in combination with the nineteenth aspect, the water treatment unit includes a component selected from the group consisting of an activated carbon unit, a sediment filter, a softening unit, a sorbent, an ultra-violet unit, a membrane filter, a distilling unit, a deionization unit and combinations thereof.

In accordance with a twenty-second aspect of the present disclosure, which may be used with in combination with any one or more of the preceding aspects, a method of preventing the formation of bacterial contamination in a water purification system comprises: passing water through a circuit of a water treatment unit, adding hydrogen peroxide to a fluid stream of the water treatment unit, circulating the fluid stream through a hydrogen peroxide decomposition catalyst, and passing the fluid stream to a renal treatment system.

In accordance with a twenty-third aspect of the present disclosure, any of the structure and functionality illustrated and described in connection with FIG. 1 may be used in combination with any one or more of the preceding aspects.

In accordance with a twenty-fourth aspect of the present disclosure, any of the structure and functionality illustrated and described in connection with FIG. 2 may be used in combination with any one or more of the preceding aspects.

It should be understood that various changes and modifications to the presently preferred embodiments described herein will be apparent to those skilled in the art. Such changes and modifications can be made without departing from the spirit and scope of the present subject matter and The invention is claimed as follows:

1. A water purification system comprising:
   a water treatment unit;
   an electrodeionization unit positioned and arranged to receive a pre-treated water stream from the water treatment unit and produce a rejected water stream and a purified water stream; and
   a hydrogen peroxide decomposition catalyst positioned and arranged to receive the rejected water stream produced by the electrodeionization unit,
   wherein the water treatment unit is positioned and arranged to receive the rejected water stream produced by the electrodeionization unit after the rejected water stream passes through the hydrogen peroxide decomposition catalyst.

2. The water purification system of claim 1, wherein the hydrogen peroxide decomposition catalyst comprises Manganese Dioxide.

3. The water purification system of claim 1, wherein the hydrogen peroxide decomposition catalyst is selected from the group consisting of Silver, Catalase, Peroxidase, Potassium Iodide, Copper (II) Oxide, Zinc Oxide, Fe(2+), Ti(3+) and combinations thereof.

4. The water purification system of claim 1 further comprising a dialyzer in fluid connection with the electrodeionization unit.

5. A renal treatment system comprising:
   a water treatment unit;
   an electrodeionization unit positioned and arranged to receive a pre-treated water stream from the water treatment unit and produce a rejected water stream and a purified water stream;
   a hydrogen peroxide decomposition catalyst positioned downstream of the electrodeionization unit to receive the rejected water stream produced by the electrodeionization unit; and
   a dialyzer in fluid connection with the electrodeionization unit,
   wherein the water treatment unit is positioned and arranged to receive the rejected water stream produced by the electrodeionization unit after the rejected water stream passes through the hydrogen peroxide decomposition catalyst.

6. The renal treatment system of claim 5, wherein the water treatment unit comprises a component selected from the group consisting of an activated carbon unit, a sediment filter, a softening unit, a sorbent, an ultra-violet unit, a membrane filter, a distilling unit, a deionization unit and combinations thereof.

7. The renal treatment system of claim 5, wherein the hydrogen peroxide decomposition catalyst comprises Manganese Dioxide.

8. The renal treatment system of claim 5, wherein the hydrogen peroxide decomposition catalyst is selected from the group consisting of Silver, Catalase, Peroxidase, Potassium Iodide, Copper (II) Oxide, Zinc Oxide, Fe(2+), Ti(3+) and combinations thereof.

9. A home hemodialysis system comprising:
   a water treatment unit;
   an electrodeionization unit positioned and arranged to receive a pre-treated water stream from the water treatment unit and produce a rejected water stream and a purified water stream;
   a hydrogen peroxide decomposition catalyst positioned downstream of the electrodeionization unit to receive the rejected water stream produced by the electrodeionization unit; and
   a dialyzer in fluid connection with the electrodeionization unit,
   wherein the water treatment unit is positioned and arranged to receive the rejected water stream produced by the electrodeionization unit after the rejected water stream passes through the hydrogen peroxide decomposition catalyst.

10. A method of performing dialysis, the method comprising:
    passing water through a water treatment unit;
    passing the water through an electrodeionization unit positioned downstream of the water treatment unit, the electrodeionization unit producing a rejected water stream and a purified water stream;
    passing the purified water stream to a dialysis treatment system;
    recirculating the rejected water stream through a hydrogen peroxide decomposition catalyst and back to the water treatment unit.

11. The method of claim 10 further comprising passing the purified water stream to a renal treatment system selected from the group consisting of hemodialysis, hemofiltration, hemodiafiltration, automated peritoneal dialysis, continuous ambulatory peritoneal dialysis and continuous flow peritoneal dialysis.

12. The method of claim 10, wherein the water treatment unit comprises a component selected from the group consisting of an activated carbon unit, a sediment filter, a softening unit, a sorbent, an ultra-violet unit, a membrane filter, a distilling unit, a deionization unit and combinations thereof.

13. A method of preventing the formation of bacterial contamination in a water purification system during dialysis, the method comprising:
    passing water through a circuit of a water treatment unit including an electrodeionization unit, the electrodeionization unit producing a rejected fluid stream and a purified fluid stream;
    adding hydrogen peroxide to the rejected fluid stream of the water treatment unit;
    circulating the rejected fluid stream through a hydrogen peroxide decomposition catalyst after adding the hydrogen peroxide;
    passing the purified fluid stream to a renal treatment system; and
    circulating the rejected fluid stream produced by the electrodeionization unit back to the water treatment unit after circulating the rejected fluid stream through the hydrogen peroxide decomposition catalyst.

* * * * *